United States Patent [19]

Folden

[11] Patent Number: 5,221,267
[45] Date of Patent: Jun. 22, 1993

[54] BREAKABLE TUBING COUPLING

[75] Inventor: Thomas I. Folden, Alamo, Calif.

[73] Assignee: Fresenius USA, Inc., Walnut Creek, Calif.

[21] Appl. No.: 713,740

[22] Filed: Jun. 11, 1991

Related U.S. Application Data

[63] Continuation-in-part of Ser. No. 621,421, Nov. 30, 1990, abandoned.

[51] Int. Cl.⁵ .............................................. A61M 5/24
[52] U.S. Cl. ...................................... 604/200; 285/4;
604/905; 604/29; 604/244
[58] Field of Search .............. 604/905, 280, 283, 284, 604/29, 49, 200, 244, 82, 87, 89, 91, 200, 206, 335, 339; 255/4

[56] References Cited

U.S. PATENT DOCUMENTS

| | | | |
|---|---|---|---|
| 3,127,892 | 4/1964 | Bellamy, Jr. et al. | 285/4 |
| 3,342,179 | 9/1967 | Ellmann | 285/4 |
| 3,841,537 | 10/1974 | Marg et al. | 222/541 |
| 3,916,929 | 11/1975 | Brown | 137/68 |
| 3,961,642 | 4/1976 | Thomas | 137/272 |
| 4,022,191 | 5/1977 | Jamshidi | 604/198 |
| 4,137,930 | 2/1979 | Scholle | 137/68 R |
| 4,181,140 | 1/1980 | Bayham et al. | 604/244 |
| 4,219,221 | 8/1980 | Webb | 604/244 |
| 4,294,247 | 10/1981 | Carter et al. | 604/244 |
| 4,340,049 | 7/1982 | Munsch | 604/905 |
| 4,386,622 | 6/1983 | Munsch | 137/1 |
| 4,398,561 | 8/1983 | Maldavs | 137/614.05 |
| 4,443,215 | 4/1984 | Smith | 604/29 |
| 4,509,911 | 4/1985 | Rosenbaum | 285/3 |
| 4,526,572 | 7/1985 | Donnan et al. | 604/29 |
| 4,620,846 | 11/1986 | Goldberg et al. | 604/28 |
| 4,668,217 | 5/1987 | Isono | 604/49 |
| 4,673,400 | 6/1987 | Martin | 604/283 |
| 4,747,822 | 5/1988 | Peabody | 604/29 |
| 4,778,447 | 10/1988 | Velde et al. | 604/29 |
| 4,810,241 | 3/1989 | Rogers | 604/28 |
| 4,820,299 | 4/1989 | Isono | 604/280 |
| 4,834,719 | 5/1989 | Arenas | 604/905 |
| 4,854,338 | 8/1989 | Grantham | 137/68.1 |
| 4,872,471 | 10/1989 | Schneider | 137/68.1 |
| 4,899,903 | 2/1990 | Miyasaka | 604/244 |
| 5,045,067 | 9/1991 | Ohnaka et al. | 604/905 |
| 5,053,003 | 10/1991 | Dadson et al. | 604/28 |

FOREIGN PATENT DOCUMENTS 2486803  1/1982  France ........................ 604/905

*Primary Examiner*—C. Fred Rosenbaum
*Assistant Examiner*—Chalin Smith
*Attorney, Agent, or Firm*—Beaton & Swanson

[57] ABSTRACT

A method and apparatus for administering dialysis including a breakable tubing coupling is provided wherein the tubing coupling is a hollow cylindrical element insertable into the lumens of distal and proximal sections of a fluid delivery tubing system, the breakable tubing coupling having a scored circumference on which the coupling can be broken and separated by application of a bending force. The breakable tubing coupling is suitable for medical applications including peritoneal dialysis tubing administration set utilization for administering fluid from fluid containers into a patient's peritoneal cavity through a peritoneal catheter and out of the peritoneal cavity and into a drain container wherein the tubing administration set having a tubing supply leg and a tubing drain leg requires means for separating the peritoneal catheter following dialysis at a predetermined location along the tubing path. The method and friable connector or breakable tubing coupling allows quick and reliable disconnection of the patient from the peritoneal dialysis tubing apparatus by eliminating the need for cutting separation of the fluid delivery line.

9 Claims, 2 Drawing Sheets

BREAKABLE TUBING COUPLING

CROSS-REFERENCE TO RELATED APPLICATION

This application is a continuation-in-part of application Ser. No. 07/621,421 entitled "PERITONEAL DIALYSIS TUBING COUPLING", filed Nov. 30, 1990, now abandoned.

FIELD OF THE INVENTION

This invention relates to breakable tubing coupling for incorporation into conduit systems utilized in medical services for transporting medical solutions and fluids as well as body fluids to and from animal and humane patients. In another aspect, the invention relates to an improved means for performing manual and automated peritoneal dialysis. More specifically, the invention is directed to an efficient and simple means for connecting and disconnecting fluid conduits that run from dialysis solution supplies to the peritoneal cavity of the patient. The invention includes friable tubing couplings which connect proximal and distal segments of conduits, the tubing couplings being breakable at specific portions of the coupling as a result of the tubing coupling having pre-stressed regions.

BACKGROUND OF THE INVENTION

The present invention is directed to improved devices and methods for reducing infection associated with the collection of body fluid from a human or animal subject and the introduction of fluids into the body.

In modern medical practice, it is often desirable either to drain fluids from or to introduce fluids into a human or animal subject under sterile conditions. For example, it is a routine practice to catheterize hospital patients for urinary or closed wound drainage. Similarly, a number of body cavities, such as the urinary bladder and the peritoneal cavity, for example, are routinely irrigated during treatment of various disorders. In these and other similar situations, the continued sterility of all associated devices used for passing fluid to and from the body may be critically important, for a contaminated device will, in many cases, lead to infection of the patient.

Two commonly used techniques for treatment of patients who have experienced significant renal failure utilize the transfer of body fluids and solutions through conduit systems to and from the patient. The traditional therapy has been hemodialysis, where the patient's blood is passed through filters that would remove the waste material from the patient's bloodstream. The second technique is peritoneal dialysis, where solutions are cycled into and out of the peritoneal cavity of the patient and wastes are removed with the spent solution.

Both techniques operate by the principles of diffusion across semipermeable membranes. In the case of peritoneal dialysis, the membrane that is used is the patient's peritoneal membrane. Although it is not as efficient as hemodialysis, peritoneal dialysis offers several advantages that has enhanced its desirability. For example, automated devices have been developed that allow a patient to undergo a dialysis treatment at night while the patient is asleep. Utilizing these automated devices allows the patient great mobility and freedom of time.

Peritoneal dialysis can be accomplished in several different modes. In Continuous Ambulatory Peritoneal Dialysis ("CAPD"), the infusion of solution into and out of the peritoneal cavity is accomplished while the patient functions normally throughout the day. The obvious disadvantages of CAPD are the cumbersome devices that must be worn by the patient. Examples of CAPD systems are presented in U.S. Pat. Nos. 5,747,822 of Peabody and 4,620,846 of Goldberg et al.

Two types of peritoneal dialysis therapies that are particularly suitable for use with automated systems are Intermittent Peritoneal Dialysis ("IPD") and Continuous Cycling Peritoneal Dialysis ("CCPD"). In IPD, large amounts of dialysis solution (up to 40 liters) are cycled through the patient's peritoneal cavity over a 4 to 24 hour period. In CCPD, the dialysis treatment is more or less continuous, with dwell times of 3 to 4 hours at night and then throughout the waking time of the patient a single charge of dialysis solution is retained within the patient. There are certain advantages to each of these two different therapy techniques.

In both IPD and CCPD, an automated dialysis apparatus operates in generally the same manner. The dialysis solution and tubing administration set is integrated with the valving, heating and control functions associated with the automated apparatus. In many of the systems, premeasured amounts of dialysis solution are either pumped or delivered by gravity flow to a heating station. At the heating station the solution is warned to body temperature in order to prevent the uncomfortable sensation of introducing room temperature or cooler solution into the peritoneal cavity. The warmed solution is then delivered from the dialysis station to the patient's peritoneal cavity via a fluid delivery line which is essentially flexible tubing connected to a catheter at the end that enters the patient's peritoneal cavity. After a period of time, "dwell periods", the solution is drained from the patient into a drain container.

In IPD, a large amount of solution is cycled in this manner over a relatively short period of time. Once treatment is completed, the patient is unencumbered for at least a few days. A disadvantage is the large amount of dialysis solution that must be utilized. Bags containing 40 liters of solution can be difficult to lift for a patient in a weakened condition.

In CCPD, the same efficiency of results is obtained by increasing the dwell time of the dialysis solution within the peritoneal cavity. The total amount of solution required can therefore be significantly reduced. The obvious disadvantage is that there is less "down time" from the treatment.

The delivery line in peritoneal therapy, as indicated above, generally includes flexible tubing to transfer fluid to and from the catheter site, a catheter to enter the peritoneal cavity, and a catheter connector between the tubing and the catheter. A releasable manual clamp is threaded onto the tubing to occlude the tubing as it is connected to the catheter through the catheter connector. Also included is a permanent manual clamp to permanently occlude the tubing when the dialysis is completed so that the tubing can be disconnected from the catheter connector without any spilling of the drained fluids. A wide variety of tubing sets are known in the art and are used in a number of different applications. For example, see the tubing administration set described in Ser. No. 425,879 by Topaz et al, assigned to the assignee of the present invention and hereby incorporated by reference.

Upon completion of the CCPD for example, it is necessary to disconnect the patient from the tubing set.

This is normally accomplished by permanently occluding the delivery line by closing the permanent manual clamp, and then cutting the tubing on the side of the permanent manual clamp away from the patient. The permanent manual clamp thereby occludes the delivery line on the patient side in order to prevent any spilling of the drained fluid. After the tubing is cut, a clamp on the catheter is used to occlude the catheter, and the stub of the tubing is removed from the catheter. When the CCPD is repeated, a new tube is connected to the catheter, the catheter clamp is loosened, and the process is repeated.

The cutting of the delivery line is normally accomplished with a pair of scissors or a knife. This, of course, necessitates that the scissors or knife be available. Moreover, because CCPD therapy is purposely designed so that it can be administered by the patient himself without the help of a nurse or other person, the scissors or knife must be located so that the patient can reach them while still connected to the tubing set.

Another problem with a system in which the delivery line is cut with a knife or scissors is that there is no indicator on the delivery line of where it should be cut. A frequent problem, therefore, is that the patient accidentally cuts the delivery line on the patient side of the clamp, thereby spilling drain fluid. Even worse, the patient sometimes accidentally cuts the catheter rather than the tubing, thereby requiring the removal of the damaged catheter and the insertion of a new catheter.

After the tubing is cut, a clamp on the catheter is used to occlude the catheter and the stub of the tubing is removed from the catheter. When the CCPD is repeated, a new tube is connected to the catheter, the catheter clamp is loosened, and the process is repeated.

A continuing dilemma exists in systems presently used in a variety of medical fluid conduit apparatus whether attended by professional assistance or manipulated by the patient. Frequently, the professional assistant is required to connect and disconnect body fluid and medical solution conduits several times a day while performing other patient care obligations simultaneously. A continuing need exists for breakable tubing coupling apparatus and methodology for both the professional assistant and the weakened patient performing self-treatment. Neither individual has the ability or the flexibility to utilize extra equipment such as knives or scissors to cut conduit or tubing. In addition, the position of the tubing cut is generally critical, thus the need for preconditioned apparatus for breakable tubing coupling applications are most desirable.

SUMMARY OF THE INVENTION

It is one feature of this invention to provide a breakable tubing coupling apparatus and methodology wherein the tubing coupling apparatus utilizes a friable section of the coupling means in a unique manner which allows for simple manual snap breakage of the coupling.

The present invention overcomes the problems of the prior art associated with the cutting of delivery conduit lines. Breakable tubing coupling utilized within a medical conduit system and methods for using same for transporting body and medical solutions are provided, the breakable tubing coupling being adapted to be incorporated into a conduit system and comprising a tubing coupling member which when responsive to manual force thereon breaks the tubing coupling connection. The tubing coupling apparatus having a friable unit or region holding the coupling member in place and joining two separate tubing members.

The apparatus and methodology of the invention is generally directed toward but not limited to tubing of medical delivery conduits inclusive of a plastic coupling toward the tubing end that goes to, for example, a catheter communicating with the patient's peritoneal cavity. The coupling divides the tubing into a segment proximal to the peritoneal cavity and a segment distal to the peritoneal cavity, the two segments being connected by the breakable tubing coupling.

The coupling has a hollow cylindrical element, one end of which is inserted into the open end of the distal tubing segment and one end of which is inserted into the open end of the proximal tubing segment. The coupling is retained in the tubing by a friction fit or solvent bond. An annular lip around the circumference of the coupling at or near its longitudinal center serves as a stop for the tubing ends. The tubing, when bended to the coupling, is positioned over the friable section which overlaps the broken segment and protects the patient from potential scratches or scrapes caused by the edges of the broken coupling. In another embodiment, the tubing ends are inserted into a cylindrical receiving chamber, i.e. a female receiving chamber for the tubing ends which provide stops for the tubing ends and provides for a friable section between the two tubing end stops. The various coupling apparatus according to the invention incorporates a friable section at a position which affords breakable separation by manual bending of the coupling. In one aspect, the coupling is scored or partially scored or in other ways pre-stressed around its circumference near the annular lip.

When peritoneal dialysis treatment is completed, and the delivery line is suitably clamped, the coupling according to the invention is easily broken by bending. In this way, no scissors or knife apparatus are needed and there is no risk that the delivery line will be cut on the wrong side of the clamp or that the catheter will be inadvertently cut.

An improved method of peritoneal dialysis treatment of the type using a tubing set having a supply leg, infusion leg and a drain leg whereby a patient having a peritoneal catheter for infusion of dialysis solution can be separated following dialysis at a predetermined location along the infusion path from the tubing set without tools or difficulty is provided. A breakable tubing coupling is achieved by inserting one end of a friable connector into a distal portion of the infusion leg of the tubing set while inserting the other end of the friable connector into a distal end of the patient's catheter. The dialysis treatment is performed by infusing the patient with dialysis solution and draining the infused solution from the patient through the catheter. Following the dialysis treatment, the patient's catheter is occluded intermediate to the patient in friable connector followed by breakage of the friable connector by bending force applied to connector through the distal ends of the catheter and infusion leg to separate the patient and his catheter from the tubing set without use of tools or assistance other than by manual breakage.

DETAILED DESCRIPTION OF THE INVENTION

Figure 1:
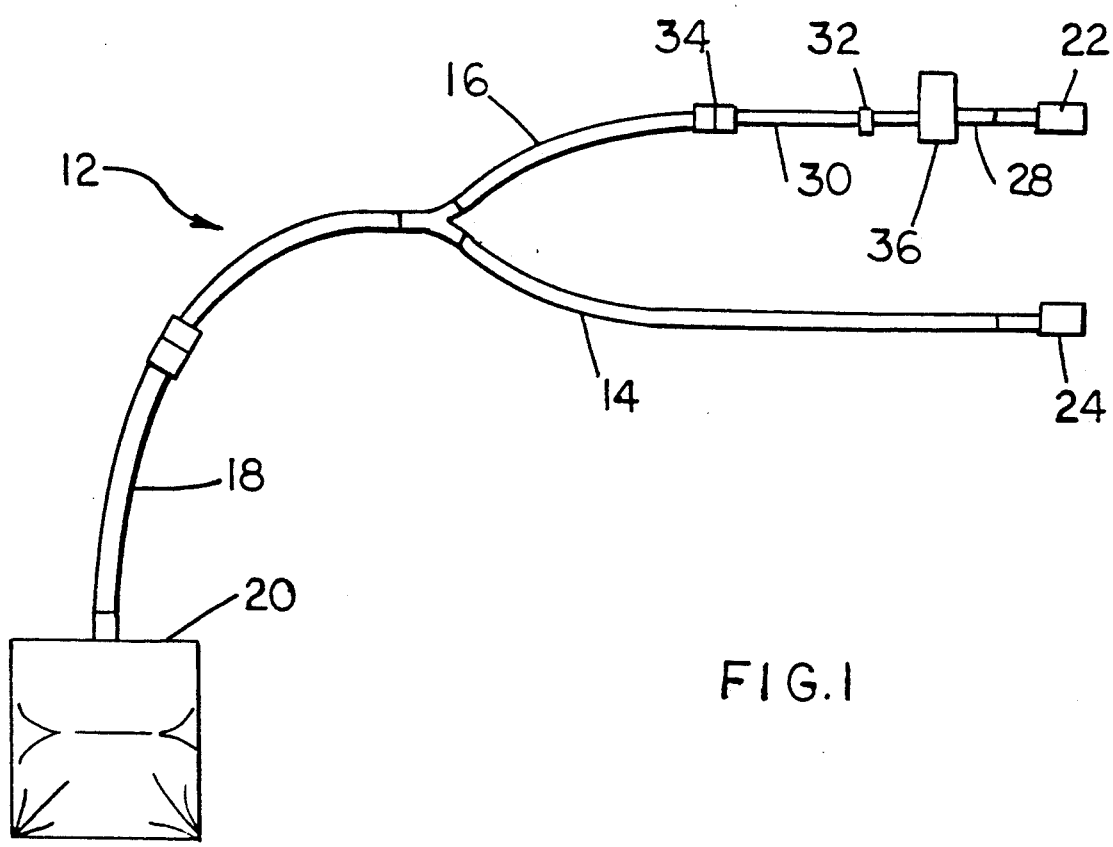
FIG. 1 is a view of a portion of a tubing administration set containing the invention, for use with an automated peritoneal dialysis apparatus.

FIG. 1 shows a portion 12 of a tubing set for use with an automated peritoneal dialysis apparatus (not shown). The tubing set portion 12 includes a fluid line 14, a fluid delivery line 16 for connection to a peritoneal catheter, a drain line 18 connected to a drain bag, and a "Y" connector for connecting the fluid line 14, fluid delivery line 16 and drain line 18. At the end of the fluid delivery line 16 is a connector 22 for connecting the fluid delivery line to a peritoneal catheter. At the end of the fluid line 14 is another connector 24 for connecting the fluid line to a set of fluid containers.

The fluid delivery line 16 includes a tube section 28 proximal to the patient's peritoneal cavity, a tube section 30 distal to the patient's peritoneal cavity and a tubing coupling 32 connecting the distal and proximal sections in the manner described below. The fluid delivery line 16 also includes a releasable manual clamp 34 on the distal tubing section 30 and a permanent manual clamp 36 on the proximal tubing section 28. The tubing is ordinary flexible plastic medical grade tubing. The releasable manual clamp 34 is an elongated open-ended biased member with a pair of clamps on its interior surface that clamps onto the tube when the member is squeezed. An edge on one of the open ends snaps into a set of serrations on the other open end to hold the clamps onto the tubing, thereby partially or entirely occluding the tubing. The edge on one of the open ends can be disengaged from the serrations in the other open end by distorting the other open end away from the edge on the first open end. Clamps of this type are well known in the art, and will not be further described here.

The permanent manual clamp 36 on the proximal tubing section 28 is also of a type that is well known in the art. Briefly, it includes two hinged halves, the first of which is slidably snapped over the tubing and the second of which mates with the first by folding onto the first through the hinge. The second half has a protrusion which collapses and thereby completely occludes the tubing when it is folded over the first half. The first half includes a pair of hooks that snap into a pair of mating slots in the second half, thereby permanently and entirely occluding the tubing.

Figure 2:
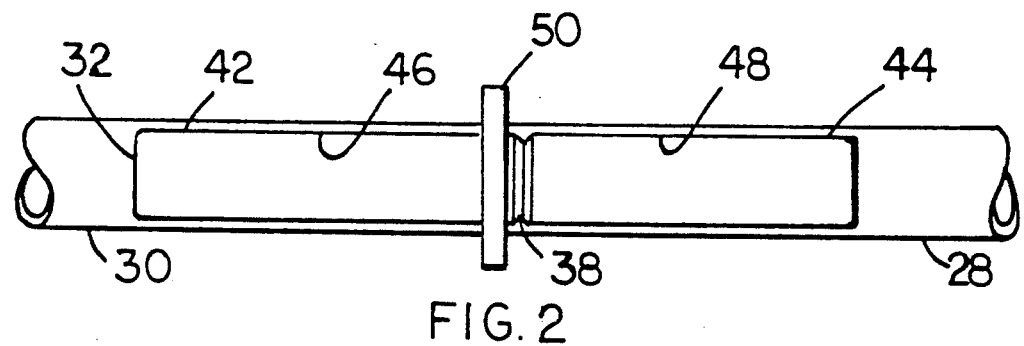
FIG. 2 is an elevated view of a coupling of the invention, shown attached to the delivery line of the tubing set of FIG. 1.
Figure 3:
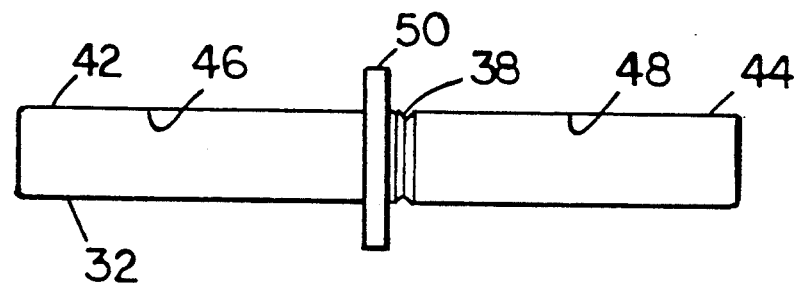
FIG. 3 is an elevated view of the coupling of FIG. 2 shown detached from the tubing set.

The tubing coupling 32 is better shown in FIG. 2 attached to the proximal tubing section 28 and distal tubing section 30, and in FIG. 3 detached from the tubing. The tubing coupling 32 includes a distal hollow cylinder 42 and a proximal hollow cylinder 44, each of which is an elongated member with a central bore 46 and 48, respectively. The outside diameter of the hollow cylinders 42 and 44 taper to a smaller diameter at each end. Preferably the maximum outside diameters are slightly greater than the inside diameter of the tubing with which it is used, so that the hollow cylinders can be pressed into the tubing to achieve a snug and watertight frictional fit between the tubing coupling and the tubing. The inside diameter of the hollow cylinders is as large as possible so that the fluid flow is not unduly restricted through the coupling, but not so large that the wall thickness of the hollow cylinders is so thin that the coupling breaks under normal operating conditions. It has been found that for use with polyvinylchloride medical grade plastic tubing, and a coupling formed from polycarbonate, these constraints can be met with an inside diameter of 0.157 inches and a maximum outside diameter of 0.242 inches and a minimum outside diameter at each end of 0.227 inches.

Positioned between the distal hollow cylinder 42 and the proximal hollow cylinder 44 of the tubing coupling 32 is a raised annular stop 50 extending around the circumference of the hollow cylinders 42 and 44. The annular stop 50 acts as a stop for the distal tubing section 30 and proximal tubing section 28, so that each is slid onto the coupling the appropriate length to achieve a secure and watertight connection. In one embodiment, each of the hollow cylinders 42 and 44 is about one inch long, and the annular stop has an outside diameter of one-half inch.

The proximal hollow cylinder 44 of the tubing coupling 32 has a scored portion 38 around its outer circumference at a location adjacent to the raised annular stop 50, so that the coupling can be broken in the manner described below. It has been found that, for a coupling wall thickness of approximately 0.040 inches, a scoring depth of approximately 0.025 inches is sufficient to allow the coupling to be broken easily, without weakening the coupling to the point that it breaks accidentally. The score may be on the distal hollow cylinder 42 rather than the proximal hollow cylinder 44. In either position, it is preferably located adjacent to the raised annular stop 50, so that neither tubing overlaps the break appreciably and prevents the coupling from separating when it is broken.

As indicated above, the tubing coupling 32 may be made from a polycarbonate, and may be injection molded. Other materials and fabrication methods will be apparent to those skilled in the art.

In operation, the tubing set is positioned so that the fluid line 14 is connected to one or more fluid containers, such as the fluid containers shown in, for example, U.S. patent application Ser. No. 425,879 filed Oct. 24, 1989. The drain container 20 is suitably located at a position generally lower than the fluid container. The fluid delivery line 16 is connected to a catheter entering the patient's peritoneal cavity. The releasable manual clamps 34 on the fluid delivery line 16 and on the fluid line 14 are opened, a releasable manual clamp on the drawing line 18 is released, and the fluid is pumped or gravity-fed from the fluid bags through the fluid line 14 and fluid delivery line 16 into the peritoneal cavity. After an appropriate dwell period, the fluid is drained by closing a clamp on the fluid line 14 to prevent backflow and opening a clamp in the drain line 18 to allow the fluid to siphon or be pumped into the drain container 20.

After fluid is removed to the drain container 20, the permanent manual clamp 36 is closed to permanently occlude the fluid delivery line 16. The fluid delivery line 16 is then separated into the proximal section 28 and distal section 30 by breaking the tubing coupling 32. The breaking of the tubing coupling 32 is accomplished by grasping each end and bending it so that it breaks cleanly along the scoring 38. The tubing proximal section 28 can be removed from the catheter after closing the catheter clamp.

Figure 4A:
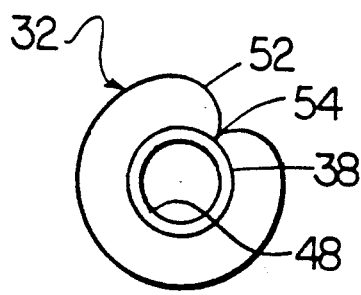
FIG. 4A is an end view of a coupling inclusive of a slotted annular lip with FIG. 4B presenting the coupling in an elevational view inclusive of the circumferential scoring near the annular lip.
Figure 4B:
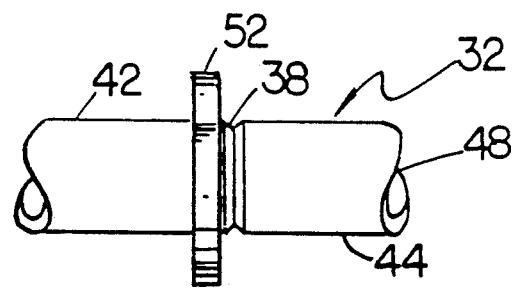
Figure 5A:
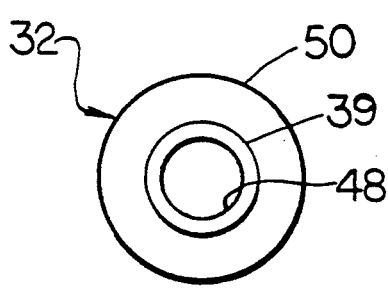
FIG. 5A presents an end view of another embodiment of the coupling inclusive of an annular lip and a jagged stress scoring shown in the elevational view of the coupling in FIG. 5B.
Figure 5B:
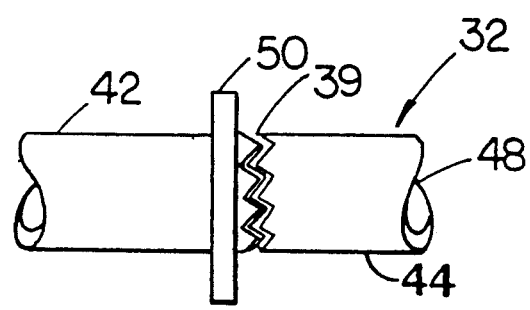
Figure 6A:
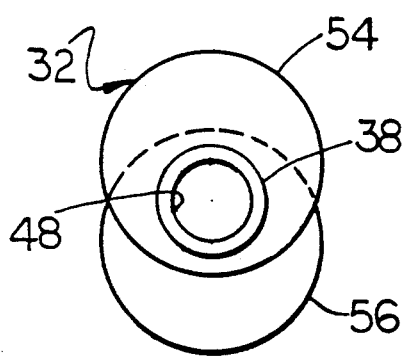
FIG. 6A presents an end view of a coupling having two irregularly shaped annular lips on opposing sides of the circumferential scoring as further shown in the elevational view of FIG. 6B.
Figure 6B:
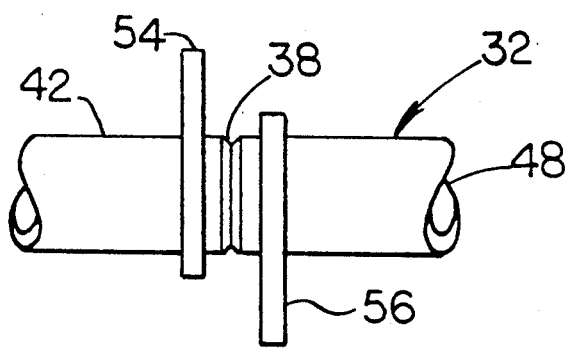

Four additional embodiments of the breakable tubing coupling according to the invention are presented in FIGS. 4A, 4B, 5A, 5B, 6A, 6B, 7A and 7B. The tubing coupling of FIG. 4A and 4B present a similar hollow cylinder 42 and 44 of approximately one inch in length, however, the annular stop is comprised of a notched annular member 52 having a notch 54 extending to the hollow cylinder 42 and 48. This structure adds additional stress to the region of the scoring 38 and enhances the breakaway manipulation of the tubing coupler. The tubing couplers of FIGS. 4, 5 and 6 provide other embodiments utilizing external annular stops and annular members 50, 52, 54 and 56. In FIG. 5, the annular stop member 50 is in cooperation with edged scoring 39 which further enhances the breakaway adaptability of the coupler. Two off-center annular members 54 and 56 on opposite sides of the scoring region 38 are provided in FIG. 5 along with the hollow cylinders 42 and 44. These two off-center annular members on opposite sides of the scoring 38 provides additional handling means for creating a clean breakaway along the scoring portion 38.

Figure 7A:
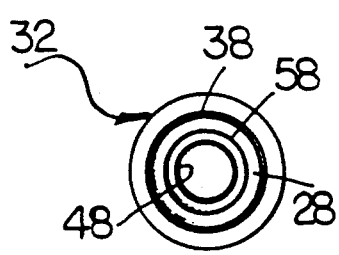
FIG. 7A provides an end view of a breakable tubing coupling having female receptacle portions for receiving tubing with a scored circumferential portion between the tubing receptacles as shown in an elevated view of FIG. 7B.
Figure 7B:
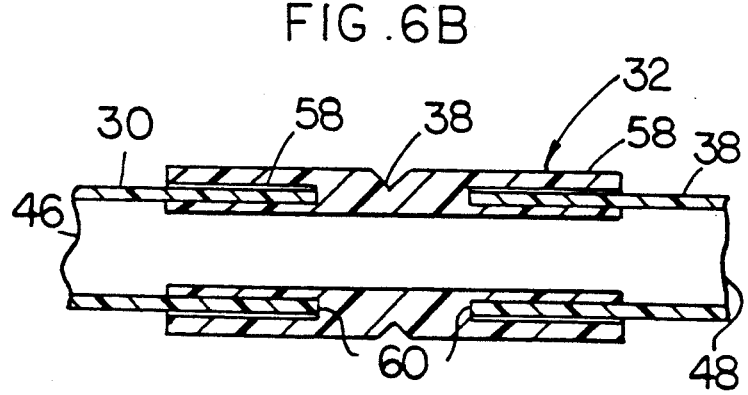

A further embodiment according to the invention of the breakable tubing coupling apparatus is shown in FIGS. 7A and 7B. This embodiment of the invention does not utilize an annular member but rather a tube receiving housing, i.e. coupling, which has scoring 38 surrounding the center portion of the coupling between two female tubing receiving chambers 58 with stops 60. Distal tubing section 30 is inserted to the coupling female tubing receiving chamber on one end of the coupling while proximal tubing section is inserted into the other end of the tubing coupling apparatus. The alternative embodiments according to the invention as illustrated in the various FIGS. 4-7 are presented for addressing possible different usage of the breakable tubing couplings in the medical arts when need for such breakable couplings are required in conduit systems for transferring body fluids and/or medicinal fluids.

The invention is also directed to a peritoneal dialysis tubing administration set for use in administrating fluid from fluid containers into a patient's peritoneal cavity through a peritoneal catheter and out of the peritoneal cavity and into a drain container. The tubing administration set has a tubing supply, and a tubing drain leg. The peritoneal catheter can be separated utilizing said following dialysis at a predetermined location along the tubing infusion leg path from the tubing set according to the invention without additional tubes through utilization of a breakaway tubing coupling means for manually separating the tubing coupling placed in the predetermined location along the infusion path which is in fluid communication with the peritoneal catheter. Such path includes a section proximal to the peritoneal catheter in a section distal to the peritoneal catheter with these proximal and distal sections being joined by the breakable tubing coupling. In the embodiment as shown in FIGS. 2 and 3 of the breakable tubing coupling, depending on materials of construction, can range from about 70 inch ounces of torque on the low end to about 125 inch ounces of torque on an upper end. The breakable tubing coupler of FIGS. 2 and 3 can be constructed with the scoring being wedge-shaped with a 60° wedge angle leaving a wall thickness of about 0.15 at the point of the wedge and the inside diameter of the central bore.

The breakable tubing coupling allows for an improved method of peritoneal dialysis of the type using a tubing set having a supply leg, an infusion leg and a drain leg whereby a patient having a peritoneal catheter for infusion of dialysis solution can be separated following dialysis at a predetermined location along the infusion path from the tubing set without any tools other than normal human dexterity. The breakable tubing coupling provide connectors having friable zones which when addressed with force to a predetermined weakened area intermediate the ends of the friable connector allows ease of breaking at a controlled location. In addition, the connectors allow mounting of tubing sets to the two ends of the connector with the tubing sets being mounted through insertion or other means with a predefined mounting overlap or connection length by stop means built into the connectors.

By separating the fluid delivery line 16 by breaking the tubing coupling 32 without the requirements of a knife, scissors or the like or any other tool at a predetermined location is of benefit to the patient and medical professional as well. There is no risk that the necessary tool is accidentally placed out of reach of the patient or that the patient might separate or sever the administration set in an incorrect position which can be of significant risk to the patient through infection. Moreover, this arrangement for separation of the fluid delivery line 16 insures that the separation will occur at the tubing coupler 32 rather than on the wrong side of a clamp or some other incorrect location. The breakable tubing couplings according to the invention provide results of a simple, inexpensive and reliable system. Although the tubing coupling is described in connection with a peritoneal dialysis tubing set and peritoneal dialysis utilization, it is readily apparent that the tubing coupling of a breakable nature can be used for other types of medical transfer of body fluids and/or medicinal fluids to and from the patient.

In FIG. 4, the annular stop member next to the scored portion can have a pie shaped type wedge cut to the tube exterior or score region increasing a stress point or tear point for breaking away the tubular connection. The scored portion can be co-molded with a different plastic material further enhancing the stress mode in the circumferential region of the tube/stop annular member. During molding, the tubing coupling device can be exposed to different rates of crystallization, i.e. polymerization under thermal control conditions at the point of stress; and the scoring need not be in a perfect ring configuration, rather a zig zag configuration around the circumference in FIG. 5 creates further stress points at the angular portions of the zig zag.

In addition, the annular stop member in FIG. 6 can be duplicated with a second member spaced apart from the first with the scored portion of the tube being placed between the two annular members. These annular members can have opposing extensions which would enhance these members as grasping means and would be of assistance in removing the broken member from either of the tubing connections. The annular stop member can be avoided as shown in FIG. 7 by using a molded member wherein the tubing is inserted into receiving portions which provide for communication of the tubular bore with a center bore of the molded article. This apparatus would be scored in various ways in a mid-region, thus allowing for a breakaway tubing coupling device which is removable from the tubing and yet without an annular stop member. The stop member in this case would be the dimensions of the tubing receiving zone. These and other embodiments of a tubing coupling provide breakaway capabilities and in addition as an alternative annular member stop means or handling means. Several of these embodiments could also provide for additional safety in avoidance of premature stress breaking or cracking of the tubing coupler during packaging, unpackaging and use.

What is claimed is:

1. A coupling for coupling two tubes, comprising an integral body with two ends and a passageway therethrough to establish fluid communication between the ends; connecting means on each of the two ends into which each of the two tubes can be inserted to establish fluid communication from each of the two tubes to each of the two ends; and scoring around the body at which the body can be broken by application of a bending force on the body to separate the two ends.

2. An apparatus, comprising: an integral body with an exterior surface, two cylindrical ends and a passageway therethrough to establish fluid communication between the ends; scoring around the body at which the body can be broken by the application of a bending force to separate the two ends; a raised portion around the exterior surface having a first side toward one end and a second side toward the other end; a first tube into which one cylindrical end is inserted up to the first side of the raised portion to sealingly establish fluid communication between the passageway and the first tube; and a second tube into which the other cylindrical end is inserted up to the second side of the raised portion to sealingly establish fluid communication between the passageway and the second tube.

3. The apparatus of claim 2, wherein the raised portion is an annular ring.

4. The apparatus of claim 3, wherein the annular ring has a cut-out portion to concentrate the bending force at the scoring around the body.

5. The apparatus of claim 4, wherein the cut-out portion is pie-shaped.

6. An improved method of peritoneal dialysis of the type using a tubing set having a supply leg, infusion leg and a drain leg, whereby a patient having a peritoneal catheter for infusion of dialysis solution can be separated following dialysis at a predetermined location along the infusion path, from the tubing set, without tools, comprising: inserting one end of a breakable connector into the infusion leg of said tubing set; inserting the other end of the breakable connector into the patient's catheter; performing the dialysis treatment of the patient by infusing the patient with dialysis solution and draining the infused solution from the patient through the catheter; occluding the patient's catheter intermediate the patient and the breakable connector; and breaking the breakable connector by bending force applied to the connector to separate the patient and his catheter from the tubing set without cutting any of the tubes.

7. The method according to claim 6, wherein the breakable connector is broken at a predetermined weakened area immediate the ends of the breakable connector to control the location of the break.

8. The method according to claim 7, wherein the step of inserting at least one of the ends of the breakable connector includes the step of limiting the amount of insertion by limiting means formed as a part of the breakable connector.

9. The method according to claim 6, wherein the breakable connector is a cylindrical element with hollow cylindrical ends insertable into tubing lumens, a central annulus to stop the insertion into the fluid tubing and a scored circumferential portion which provides a breaking position on the connector upon application of a bending force.

* * * * *